(12) United States Patent
Lima et al.

(10) Patent No.: US 11,510,771 B2
(45) Date of Patent: Nov. 29, 2022

(54) IMPLANTABLE ARTIFICIAL BRONCHUS

(71) Applicant: Pulmair Medical, Inc., San Diego, CA (US)

(72) Inventors: Marcelo G. Lima, Del Mar, CA (US); Murilo Pundek Rocha, Sao Paulo (BR); Randall L Brase, San Diego, CA (US)

(73) Assignee: Pulmair Medical, Inc., San Diego, CA (US)

( * ) Notice: Subject to any disclaimer, the term of this patent is extended or adjusted under 35 U.S.C. 154(b) by 0 days.

(21) Appl. No.: 17/294,839

(22) PCT Filed: Nov. 19, 2019

(86) PCT No.: PCT/US2019/062132
§ 371 (c)(1),
(2) Date: May 18, 2021

(87) PCT Pub. No.: WO2020/106675
PCT Pub. Date: May 28, 2020

(65) Prior Publication Data
US 2022/0015889 A1 Jan. 20, 2022

Related U.S. Application Data

(60) Provisional application No. 62/769,104, filed on Nov. 19, 2018, provisional application No. 62/805,568, filed on Feb. 14, 2019.

(51) Int. Cl.
*A61F 2/04* (2013.01)
*A61B 1/00* (2006.01)
(Continued)

(52) U.S. Cl.
CPC ............ *A61F 2/04* (2013.01); *A61B 1/00154* (2013.01); *A61B 1/2676* (2013.01); *A61F 2/962* (2013.01);
(Continued)

(58) Field of Classification Search
CPC ...... A61F 2/04; A61F 2/962; A61F 2002/043; A61F 2002/9528; A61B 1/00154; A61B 1/2676; A61B 17/242
(Continued)

(56) References Cited

U.S. PATENT DOCUMENTS 6,305,436 B1 * 10/2001 Andersen ............... D04B 15/14
140/89
10,070,977 B2 * 9/2018 Holzer .................... A61L 31/10
(Continued)

FOREIGN PATENT DOCUMENTS

JP      200655330 A    3/2006
WO     2007047151 A1   4/2007
(Continued)

OTHER PUBLICATIONS

International Search Report and Written Opinion dated Feb. 5, 2020 for International Patent Application No. PCT/US2019/062132, 10 pages.
(Continued)

*Primary Examiner* — Suzette J Gherbi
(74) *Attorney, Agent, or Firm* — Morgan Lewis & Bockius LLP

(57) ABSTRACT

An implantable artificial bronchus including a body having a proximal upper opening and a distal lower opening. The distal lower opening being in fluid communication with the proximal upper opening, and the body at least partially tapering along a length toward the distal lower opening. The body having a plurality of side openings configured to allow
(Continued)

air to enter into and exit the implantable artificial bronchus through the body. A length of the body is greater than 4 times the size of a largest diameter of the body, and the diameter of the proximal upper opening is larger than a diameter of the distal lower opening.

29 Claims, 12 Drawing Sheets

(51) Int. Cl.
    *A61B 1/267*     (2006.01)
    *A61F 2/962*     (2013.01)
    *A61F 2/95*     (2013.01)

(52) U.S. Cl.
    CPC . *A61F 2002/043* (2013.01); *A61F 2002/9528* (2013.01); *A61F 2210/0014* (2013.01); *A61F 2230/0067* (2013.01); *A61F 2250/0098* (2013.01)

(58) Field of Classification Search
    USPC .................................................. 623/1.15, 9
    See application file for complete search history.

(56) References Cited

U.S. PATENT DOCUMENTS

| | | | |
|---|---|---|---|
| 10,314,685 B2* | 6/2019 | McMahon | A61F 2/04 |
| 10,806,560 B2* | 10/2020 | Rocha | A61F 2/2476 |
| D902,407 S * | 11/2020 | Lima | D24/155 |
| 11,096,773 B2* | 8/2021 | Rocha | A61F 2/2476 |
| 2005/0273160 A1* | 12/2005 | Lashinski | A61F 2/2436 |
| | | | 604/9 |
| 2008/0072914 A1* | 3/2008 | Hendricksen | A61F 2/2476 |
| | | | 128/207.16 |
| 2009/0138070 A1* | 5/2009 | Holzer | A61F 2/90 |
| | | | 623/1.42 |
| 2010/0234937 A1* | 9/2010 | Wang | A61B 17/12104 |
| | | | 623/1.18 |
| 2013/0184809 A1* | 7/2013 | Stinson | A61F 2/966 |
| | | | 623/1.38 |
| 2013/0197657 A1* | 8/2013 | Anca | A61F 2/07 |
| | | | 623/23.7 |
| 2014/0288588 A1 | 9/2014 | Lam et al. | |
| 2015/0045882 A1* | 2/2015 | Fox | A61F 2/04 |
| | | | 623/9 |
| 2015/0045908 A1 | 2/2015 | McMahon | |
| 2015/0051709 A1* | 2/2015 | Vasquez | A61B 17/12036 |
| | | | 623/23.65 |
| 2015/0065999 A1* | 3/2015 | Von Segesser | A61B 17/3439 |
| | | | 604/523 |
| 2016/0022449 A1* | 1/2016 | Lim | A61F 2/04 |
| | | | 623/9 |
| 2016/0338822 A1* | 11/2016 | Rocha | A61F 2/2476 |
| 2017/0367810 A1* | 12/2017 | Tanaka | A61B 17/1214 |
| 2018/0214141 A1* | 8/2018 | Mendez | A61B 17/0057 |
| 2018/0344445 A1* | 12/2018 | Rocha | A61F 2/04 |
| 2019/0150936 A1* | 5/2019 | Mathis | A61B 17/122 |

FOREIGN PATENT DOCUMENTS

| | | | | |
|---|---|---|---|---|
| WO | 2018027145 A1 | | 2/2018 | |
| WO | WO-2020106675 A1 | * | 5/2020 | A61F 2/04 |

OTHER PUBLICATIONS

Examination Report for corresponding Australian Application No. 2019385783 dated Feb. 8, 2022, 4 pages.

Office Action for corresponding Japanese Patent Appln. No. 2021-525100 dated Apr. 27, 2022, 24 pages.

English translation of "Examination Guidelines for Patent and Utility Model in Japan", Part III, Chapter 1, 3.1.

English translation of "Examination Handbook for Patent and Utility Model in Japan", Part II, 2203.

* cited by examiner

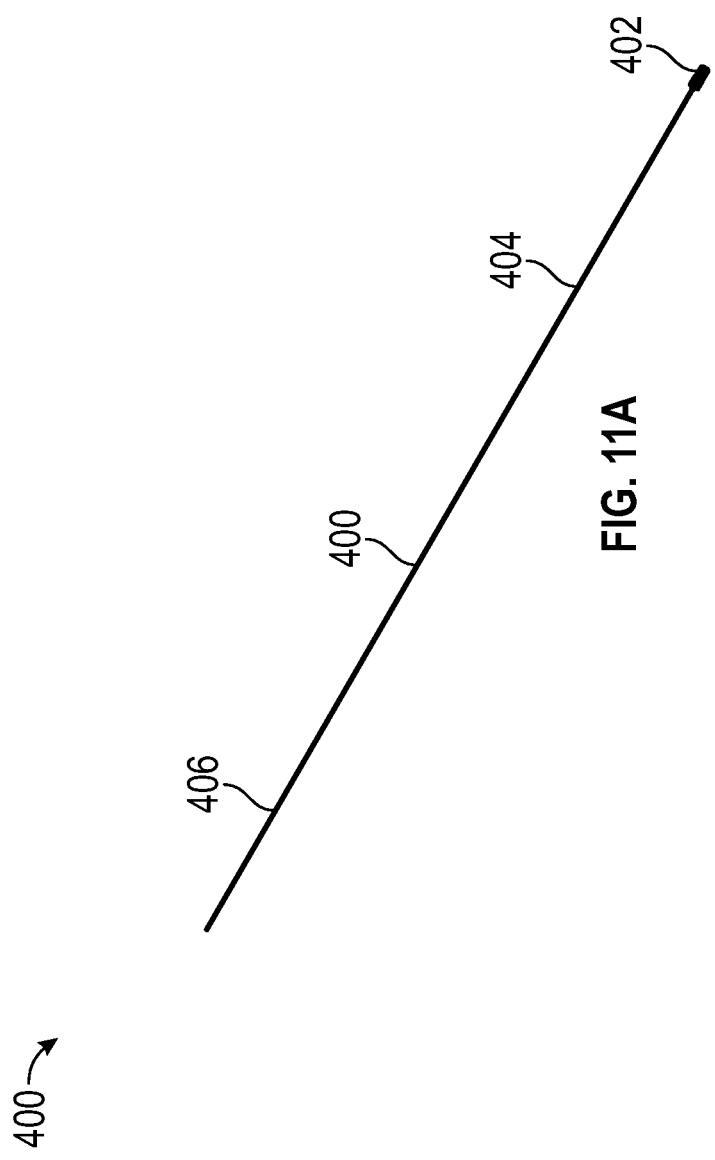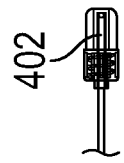
FIG. 11A
FIG. 11B

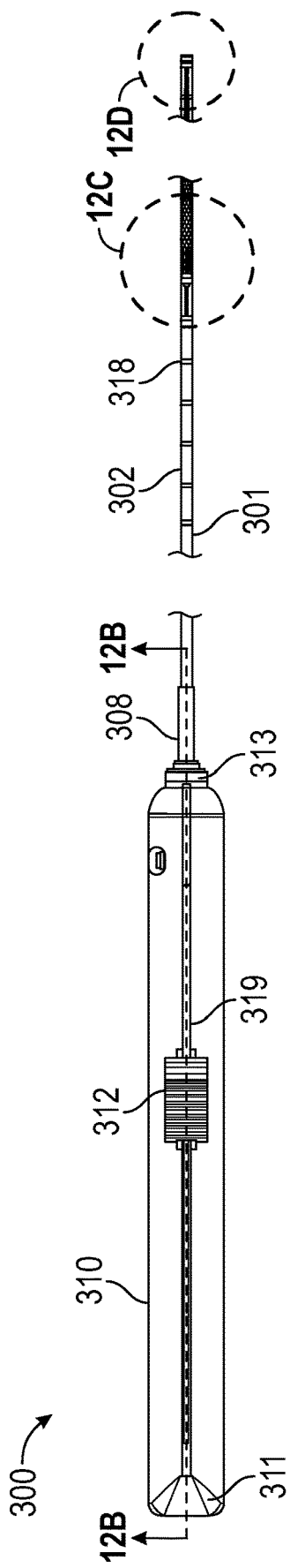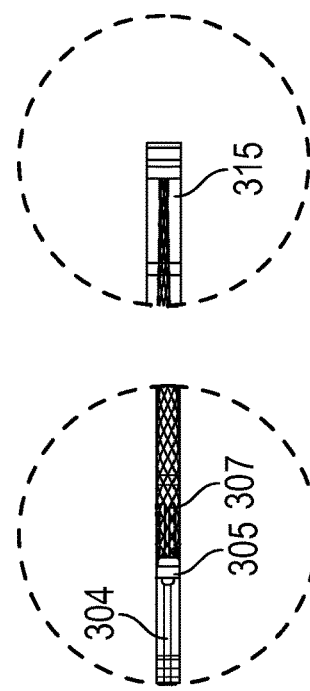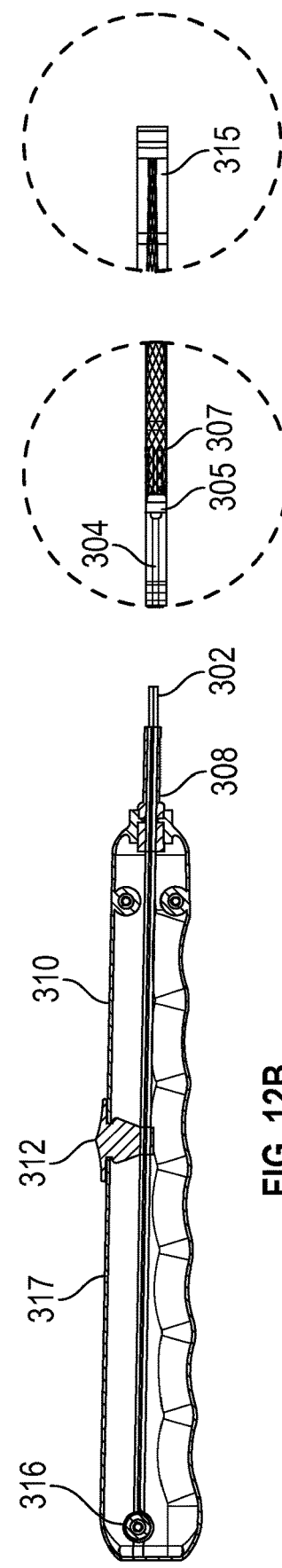

# IMPLANTABLE ARTIFICIAL BRONCHUS

CROSS REFERENCE TO RELATED APPLICATIONS

This application is a U.S National Phase of International Application No. PCT/US2019/062132 filed on Nov. 19, 2019, which claims the benefit of U.S. Provisional Patent Application No. 62/769,104 filed Nov. 19, 2018 entitled "Implantable Artificial Bronchus" and U.S. Provisional Patent Application No. 62/805,568 filed Feb. 14, 2019 entitled "Implantable Artificial Bronchus", each of which is incorporated by reference herein in its entirety.

FIELD OF THE INVENTION

The present invention generally relates to an implantable artificial bronchus and methods of implanting the same for treatment of pulmonary emphysema and chronic obstructive pulmonary disease (COPD).

BACKGROUND OF THE INVENTION

Chronic obstructive pulmonary disease (COPD) can result in long-term breathing problems, poor airflow, shortness of breath, coughing, and sputum production. Pulmonary emphysema is a form of COPD and is experienced by a majority of individuals who suffer from COPD.

Pulmonary emphysema is characterized by the permanent enlargement of the gas exchange units in the lungs, acini, due to breakdown of the lung tissue and destruction of the alveolar walls. This gradual and irreversible degradation of the lung tissue leads to the loss of elastic capacity, lung recoil, expressed by the inability to expel inspired air. Further, the degradation of lung tissue contributes to the poor airflow, and thus, the poor absorption and release of respiratory gases.

Current treatments for pulmonary emphysema are limited and only provide symptomatic improvements. For example, a majority of current medications only treat the inflammatory component. Further, supplemental oxygen for hypoxic patients and pulmonary rehabilitation are the only medical treatments that have shown to improve mortality in severe cases of COPD. Surgical approaches, such as surgical lung volume reduction, is only indicated for a small proportion of patients and the procedure is invasive as it requires removing diseased, emphysematous lung tissue. Other methods, such as bronchoscopic techniques and stents, are currently being developed for treatment of severe COPD and have made progress over the past decade. However, these methods either do not allow bi-directional airflow, do not go deep enough within the distal levels of the respiratory bronchioles, or do not provide long term improvements to patients, for example, due to premature closing of the implanted stent or accelerating the damage to the patient.

Accordingly, there is a need for a more effective treatment for pulmonary emphysema and COPD which is minimally invasive, which includes bi-directional airflow, is able to go into deeper generations of respiratory bronchioles and does not result in more damage to the patient long term or trigger healing mechanisms within the lung.

BRIEF SUMMARY OF THE INVENTION

Embodiments of the present invention are directed to an implantable artificial bronchus, including a body having a proximal upper opening and a distal lower opening in fluid communication with the proximal upper opening, the body at least partially tapering along a length of the body toward the distal lower opening and having a plurality of side openings configured to allow air to enter into and exit the implantable artificial bronchus through the body. A length of the body is greater than 4 times the size of a largest diameter of the body and, a diameter of the proximal upper opening is larger than a diameter of the distal lower opening.

In some embodiments, the body may include a proximal portion, a first middle portion, a second middle portion, and a distal portion, the proximal portion being tapered towards a central axis of the body. The first middle portion and the second middle portion may be disposed between the proximal portion and the distal portion. The first middle portion may be proximate the proximal portion and the second middle portion being proximate the distal portion. The first middle portion may have a first taper and the second middle portion may have a second taper, the second taper may be larger than the first taper.

In some embodiments, a diameter of the first middle portion may be greater than a diameter of the proximal portion, a diameter of the second middle portion, and a diameter of the distal portion. The diameter of the distal portion may be less than the diameter of the proximal portion, the diameter of the first middle portion, and the diameter of the second middle portion. The diameter of the first middle portion may be equal to or less than the largest diameter of the body. The diameter of the second middle portion may constantly decreases along the length of the body from the first middle portion to the distal portion. The diameter of the distal portion may be substantially the same proximate the second middle portion and proximate distal lower opening.

In some embodiments, the proximal portion may flares out from the proximal upper opening to the first middle portion.

In some embodiments, a maximum diameter of the body may be greater than the diameter of the proximal upper opening.

In some embodiments, the body may be a web comprised of the single fiber forming a lattice structure, the single fiber may have ends woven together proximate a middle portion of the body. The single fiber may be coated with at least one of silicone or polymer.

In some embodiments, the diameter of the proximal upper opening is greater than twice the diameter of the distal lower opening.

In some embodiments, in an implanted state the body may be configured to curve in a first radial direction along a first length of the body and a second radial direction opposite the first radial direction along a second length of the body.

In some embodiments, the plurality of side openings may include an angle ranging between approximately 130° proximate the proximal upper opening and 20° proximate the distal lower opening.

In some embodiments, the implantable artificial bronchus may include at least one retrieval loop coupled to the body at the proximal upper opening. The at least one retrieval loop may extend from the proximal upper opening in a direction substantially parallel to a central axis of the body.

In some embodiments, the implantable artificial bronchus includes at least one radiopaque marker disposed on the body.

In some embodiments, the body may have a maximum diameter of approximately 6 mm to approximately 12 mm. The body may be comprised of PEEK. The body may be comprised of NiTiNOL. Further, the body may include a single fiber arranged in an alternating cross-weaving pattern.

In some embodiments, the implantable artificial bronchus may not include a valve or a nozzle coupled to the body.

Another embodiment of the present invention may provide an implantable artificial bronchus including a body having a proximal upper opening and a distal lower opening in fluid communication with the proximal upper opening, the proximal upper opening tapering towards a central axis of the body. The body may constantly taper from a portion proximate the proximal upper opening toward a portion proximate the distal lower opening, and may have a plurality of side openings configured to allow air to enter into and exit the implantable artificial bronchus through the body. The body may include a proximal portion being tapered toward a central axis of the body, a first middle portion having a first middle taper, a second middle portion having a second middle taper larger than the first middle taper, and a distal portion having a constant distal diameter. The first middle portion and the second middle portion may be disposed between the proximal portion and the distal portion. A diameter of the proximal upper opening may be at least twice as large as a diameter of distal lower opening, and the diameter of the proximal upper opening may be less than a maximum diameter of the body, the maximum diameter of the body being proximate the proximal upper opening. In an implanted state the body may be configured to curve in a first radial direction along a first length of the body and a second radial direction opposite the first radial direction along a second length of the body.

Another embodiment of the present invention may provide a method of promoting lung disinsufflation, the method including inserting a catheter distally into a respiratory passageway of a patient's lung, the catheter containing the implantable artificial bronchus compressed within the catheter, and withdrawing the catheter proximally relative to the implantable artificial bronchus, unsheathing the implantable artificial bronchus, causing the implantable artificial bronchus to naturally expand and remain in the respiratory passageway, the implantable artificial bronchus configured to promote enlargement of the respiratory passageway.

In some embodiments, the catheter may be a guide catheter and the implantable artificial bronchus may extend into a bronchiole passageway.

Another embodiment of the present invention may provide a method of delivering the implantable artificial bronchus to an air passageway, the method including inserting the implantable artificial bronchus into a delivery device. The delivery device may include a handle having a proximal end, a distal end, an outer surface, and an actuator movable about the outer surface. The delivery device may further include a delivery portion including an outer sheath and a delivery wire, the outer sheath coupled to the actuator of the handle and extending out of the distal end of the handle, the outer sheath having a distal end and at least one slot, wherein the implantable artificial bronchus is inserted into the delivery device via the distal end. The delivery wire may be coupled to a proximal end of the handle and extending out of the distal end of the handle and into the outer sheath such that the delivery wire is disposed within the outer sheath, the delivery wire including a stopping member, wherein the stopping member is disposed proximate the implantable artificial bronchus after insertion of the implantable artificial bronchus into the delivery device. The method further includes inserting the delivery portion of the delivery device into a bronchoscope such that the outer sheath is disposed within a working channel of the bronchoscope, advancing the delivery portion through the bronchial passage via the bronchoscope, retracting the outer sheath, via the actuator, exposing the delivery wire and the implantable artificial bronchus, causing the implantable artificial bronchus to naturally expand and remain in the bronchial passage, and removing the delivery device from the bronchial passage through the working channel of the bronchoscope.

In some embodiments, inserting the implantable artificial bronchus into the delivery device includes threading a suture through at least one proximal loop of the implantable artificial bronchus, pulling on the suture to cause the implantable artificial bronchus to collapse, inserting the suture and the implantable artificial bronchus through the distal end of the outer sheath, and removing the suture from the implantable artificial bronchus and the delivery device, via the at least one slot, such that the implantable artificial bronchus remains in the delivery device.

BRIEF DESCRIPTION OF THE SEVERAL VIEWS OF THE DRAWINGS

The foregoing summary, as well as the following detailed description of embodiments of the implantable artificial bronchus, will be better understood when read in conjunction with the appended drawings of exemplary embodiments. It should be understood, however, that the invention is not limited to the precise arrangements and instrumentalities shown.

FIGS. 11A-B are illustrations of an exemplary measuring catheter in accordance with one embodiment of the present invention; and FIGS. 12A-D are illustrations of an exemplary delivery device in accordance with one embodiment of the present invention.

DETAILED DESCRIPTION OF THE EXEMPLARY EMBODIMENTS OF THE INVENTION

Figure 1:
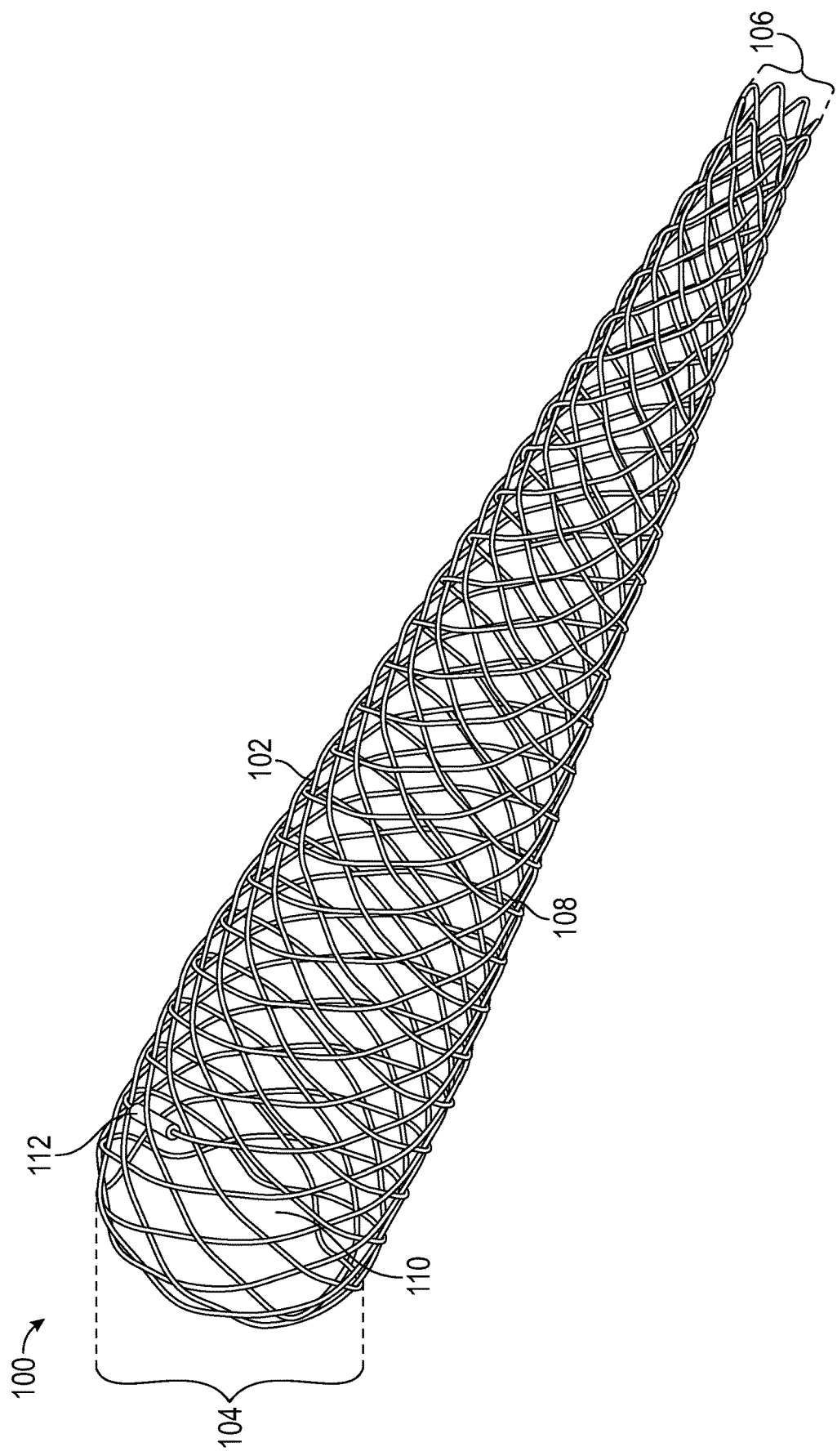
FIG. 1 is a perspective view of an exemplary implantable artificial bronchus in accordance with one embodiment of the present invention.
Figure 2:
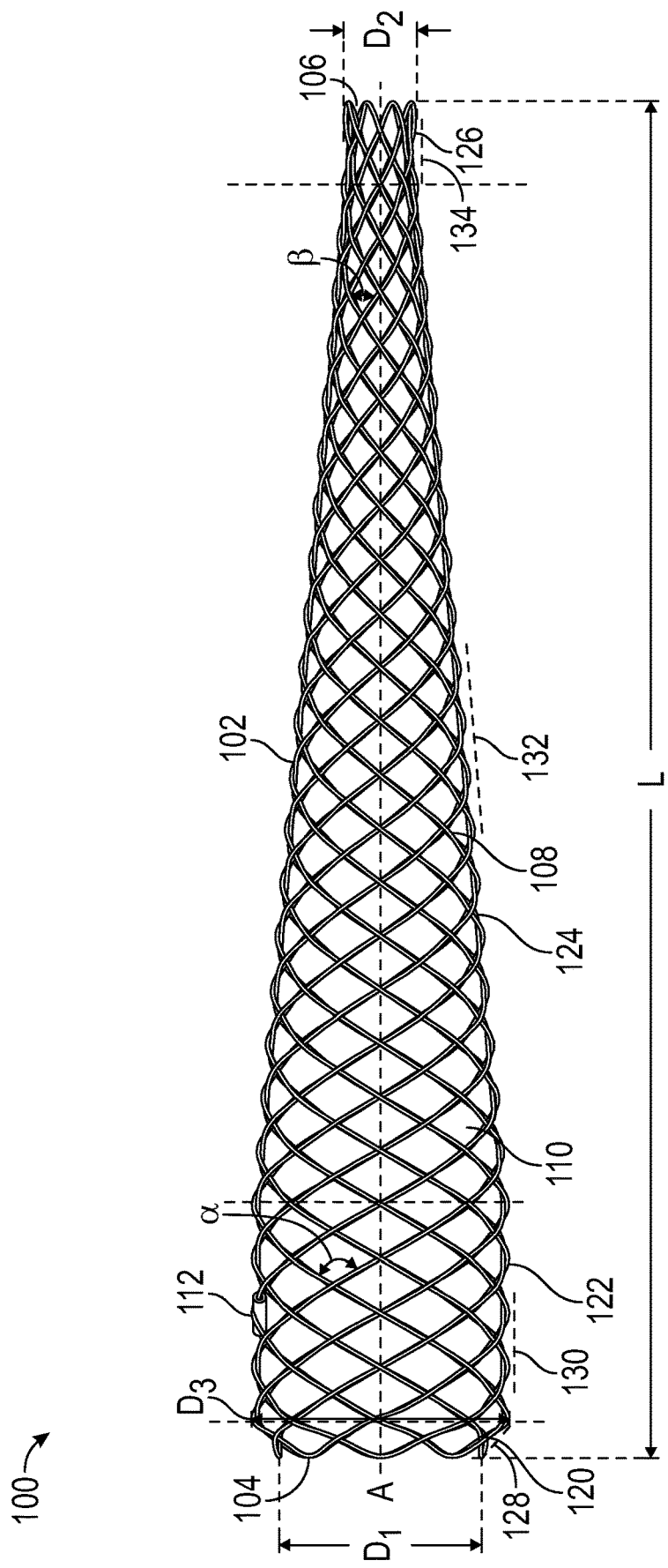
FIG. 2 is a side view of the implantable artificial bronchus shown in FIG. 1.

Exemplary embodiments of the present invention provide an implantable artificial bronchus and methods of implanting the same. In use, implantable artificial bronchus 100 may facilitate the opening of airways within individuals with COPD and pulmonary emphysema. Specifically, implantable artificial bronchus 100 may allow for air trapped within the respiratory passageways, such as bronchi and bronchioles, to exit by opening up, and keeping open, the respiratory passageways. The implantation of implantable artificial bronchus 100 in the respiratory passageway may keep the walls of the bronchi and bronchioles from restricting thereby allowing airflow through the passageways. As shown in FIGS. 1 and 2, implantable artificial bronchus 100 may include body 102, proximal upper opening 104, distal lower opening 106, wire or fiber 108, and side openings 110. Body 102 may be disposed between proximal upper opening 104 and distal lower opening 106, and may be comprised of a fiber 108. Implantable artificial bronchus 100 may be at least partially tapered to allow for the insertion into the bronchi and penetration of implantable artificial bronchus 100 within distal bronchioles that increasingly become more narrow. For example, implantable artificial bronchus 100 may be deployed within the respiratory passageway such that proximal upper opening 104 is disposed within the bronchi, and distal lower opening 106 is able to reach as close as possible to respiratory bronchioles at levels 9 to 15 (terminal bronchioles).

As shown in FIGS. 1 and 2, implantable artificial bronchus 100 may be comprised of body 102. In one embodiment, body 102 is unobstructed and does not include a valve coupled to body 102. Body 102 of implantable artificial bronchus 100 may be generally cylindrical towards proximal upper opening 104, conical for a majority of body 102, and generally cylindrical towards distal lower opening 106. Body 102 may have maximum diameter $D_3$, and may be tapered along length L of body 102 proximate proximal upper opening 104, and between proximal upper opening 104 and distal lower opening 106. For example, body 102 may include proximal portion 120, first middle portion 122, second middle portion 124, and distal portion 126. First middle portion 122 and second middle portion 124 may be disposed between proximal portion 120 and distal portion 126, with first middle portion 122 being proximate proximal portion 120 and second middle portion being proximate distal portion 126. Proximal portion 120 may taper towards central axis A and may have slope 128, which may be between approximately 40-50 degrees relative to central axis A and may slope towards proximal upper opening 104. First middle portion 122 may have a greater diameter than proximal portion 120 and may be generally cylindrical in shape. For example, first middle portion 122 may have a generally uniform diameter or may have a slight taper towards central axis A. First middle portion 122 may have slope 130, which may be between approximately 2-4 degrees relative to central axis A and may slope towards distal lower opening 106. First middle portion 122 having a greater diameter than proximal portion 120 allows first middle portion 122 to engage the walls of the bronchi, preventing them from collapsing, and securing implantable artificial bronchus 100. For example, first middle portion 122 may allow implantable artificial bronchus 100 to be anchored proximally at levels 3 or 4 of the bronchi. In an embodiment, the diameter of first middle portion 122 may be substantially the same as maximum diameter $D_3$. In another embodiment, maximum diameter $D_3$ may be disposed between proximal portion 120 and first middle portion 122. Proximal portion 120 and first middle portion 122 may be disposed within the bronchi. Second middle portion 124 may be conical in shape. Second middle portion 124 may taper towards central axis A and may have a gradually decreasing diameter. Second middle portion 124 may have slope 132, which may be between approximately 10-12 degrees relative to central axis A and may slope towards distal lower opening 106. The diameter of second middle portion 124 may be less than the diameter of first middle portion 122 and may taper at a faster rate compared to first middle portion 122. A section of second middle portion 124 proximate first middle portion 122 may be disposed in the bronchi. Second middle portion 124 may extend into the bronchioles and may taper until distal portion 126. Distal portion 126 may be cylindrical in shape and may have a diameter less than second middle portion 124, first middle portion 122, and proximal portion 120. Distal portion 126 may be disposed within the bronchioles. In an embodiment, distal portion 126 does not include any tapering such that the diameter of distal portion 126 proximate second middle portion 124 is the same as the diameter proximate distal lower opening 106. For example, distal portion 126 may have an internal dimeter of approximately 2 mm, which may be substantially the same as diameter $D_2$ of distal lower opening 106. In an embodiment, distal portion 126 tapers towards central axis A and may have slope 134, which may be between approximately 1-3 degrees relative to central axis A and may slope towards distal lower opening 106. In yet another embodiment, distal portion 126 may flare out, away from central axis A. For example, distal portion 126 may flare out to prevent inserting implantable artificial bronchus 100 too deeply within the bronchioles. Slopes 128, 130, 132, and 134 may be between approximately 0 degrees and 15 degrees. Slopes 128, 130, 132, and 134 may vary based on length L of body 102. For example, slope 132 of second middle portion 124 may be approximately 4.3 degrees when length L is approximately 50 mm and may be approximately 2.7 degrees when length L is approximately 80 mm. In some embodiments, it is advantageous to have a greater degree of taper for slopes 128,130, 132, and 134 placed on the placement of implantable artificial bronchus.

In one embodiment, the shape and length of body 102 allows implantable artificial bronchus 100 to be inserted into a respiratory passageway to keep the respiratory passageways open in respiratory bronchioles beyond level 15, close to alveoli (>15 levels), resulting in trapped air exiting the lower generations. According to an embodiment of the present invention, length L of body 102 may be greater than 4 times maximum diameter $D_3$ of body 102. For example, maximum diameter $D_3$ of body 102 may be between 9.5 millimeters and 10.5 millimeters, and maximum length L of body 102 may be 50 millimeters or 80 millimeters. In some embodiments, length L of body 102 may be greater than 2.5, 3, 3.5, 4.5, 5.5, 6, 6.5, 7, 7.5, 8, 8.5, 9, 9.5, or 10 times maximum diameter $D_3$ of body 102. Maximum diameter $D_3$ of body 102 being 9 millimeters may allow for implantable artificial bronchus 100 to be deployed within 6-8 millimeter bronchi. However, maximum diameter $D_3$ may be any size desired such as approximately 6 mm, approximately 7 mm, approximately 8 mm, approximately 10 mm, approximately 11 mm, or approximately 12 mm, and maximum length L of body 102 may be greater than 80 millimeters, less than 50 millimeters, or in between 50 and 80 millimeters. In one embodiment, maximum diameter $D_3$ of implantable artificial bronchus 100 is manufactured to be approximately 10.5 mm, which is reduced to approximately 8 mm or smaller upon deployment within the respiratory passageway. In use, maximum diameter $D_3$ may vary between 25-50% based on the breathing cycle, and dilation and constriction of the respiratory passageways. Maximum diameter $D_3$ may also vary due the flexibility of implantable artificial bronchus 100. For example, maximum diameter $D_3$ may increase or decrease based on changes of the diameter of the bronchus, such as during a breathing cycle. Maximum length L of body 102 may vary in length to be sized to fit within shorter or longer respiratory passageways. For example, maximum length L of body 102 may be longer to penetrate to deeper, thinner respiratory bronchioles.

In an embodiment of the present invention, a kit may be provided which includes multiple implantable artificial bronchi 100 having various maximum lengths L of body 102. For example, a kit may include one implantable artificial bronchus 100 where maximum length L of body 102 is 50 millimeters, another implantable artificial bronchus 100 where maximum length L of body 102 is 80 millimeters, and a third implantable artificial bronchus 100 where maximum length L of body 102 is greater than 80 millimeters. A surgeon may choose one implantable artificial bronchus 100 from the kit having a specific maximum length L of body 102 based on the anatomy of a patient. Further, maximum diameter $D_3$ of body 102 may be located at a portion proximate to proximal upper opening 104 and may be sized to press against the bronchi walls of the upper levels of the respiratory passageways. Maximum diameter $D_3$ being located proximate to proximal upper opening 104 may prevent or reduce proximal upper opening 104 from contacting the bronchi walls, which may assist in the adjustment, retrieval, and removal of implantable artificial bronchus 100 via proximal upper opening 104.

According to an embodiment of the present invention, the diameter of body 102 may decrease from a portion of body 102 proximate proximal upper opening 104 to distal lower opening 106. For example, body 102 may constantly taper from a portion proximate to proximal upper opening 104 toward the distal lower opening 106. Body 102 may constantly taper from maximum diameter $D_3$ of body 102, which may be approximately 9.5 mm, to diameter $D_2$ of distal lower opening 106, which may be approximately 2 mm. In other embodiments, body 102 tapers slightly initially from the proximal end, more dramatically in the middle, and then slightly or not at all toward the distal end. For example, body 102 may constantly taper from maximum diameter $D_3$ to an area of body 102, for example, located approximately 2 mm from distal lower opening 106. Thereafter, body 102 may be flat, with no taper, for the rest of approximately 2 mm length. The rate of taper of body 102 may vary based on maximum length L of body 102. For example, the rate of taper of body 102 may be greater if maximum length L of body 102 is lower.

Referring to FIGS. 1 and 2, proximal upper opening 104 may be in fluid communication with distal lower opening 106 to allow for bi-directional airflow in and through implantable artificial bronchus 100. Proximal upper opening 104 may have diameter $D_1$ and distal lower opening 106 may have diameter $D_2$. According to some embodiments, diameter $D_1$ of proximal upper opening 104 may be larger than diameter $D_2$ of distal lower opening 106. For example, diameter $D_1$ of proximal upper opening 104 may be greater than twice diameter $D_2$ of distal lower opening 106. In another example, diameter $D_1$ of proximal upper opening 104 may be approximately 7.5 mm and diameter $D_2$ of distal lower opening 106 may be approximately 2 mm. However, diameter $D_1$ of proximal upper opening 104 may be between approximately 5 mm and 14 mm, between approximately 6 mm and 13 mm, between approximately 7 mm and 12 mm, between approximately 8 mm and 11 mm, or between approximately 9 mm and 10 mm. Further, diameter $D_2$ may be between approximately 0 mm and 6 mm, between approximately 1 mm and 5 mm, or between approximately 2 mm and 4 mm. In practice, diameter $D_1$ of proximal upper opening 104 and diameter $D_2$ of distal lower opening 106 may be sized to fit within and reach various respiratory bronchi and bronchiole levels, such as distal bronchioles. For example, in one embodiment, diameter $D_2$ of distal lower opening 106 may be sized to be between approximately 2 mm and approximately 3 mm to fit within and reach respiratory bronchioles at level 15, which have a diameter between approximately 2.5 mm and approximately 3 mm. Further, in another embodiment, diameter $D_2$ of distal lower opening may be smaller than approximately 2 mm, such as 1.5 mm, to fit within and reach deeper levels of respiratory bronchioles, such as respiratory bronchioles level 16-18, which are approximately 1.5 to approximately 1 mm in diameter.

Figure 3:
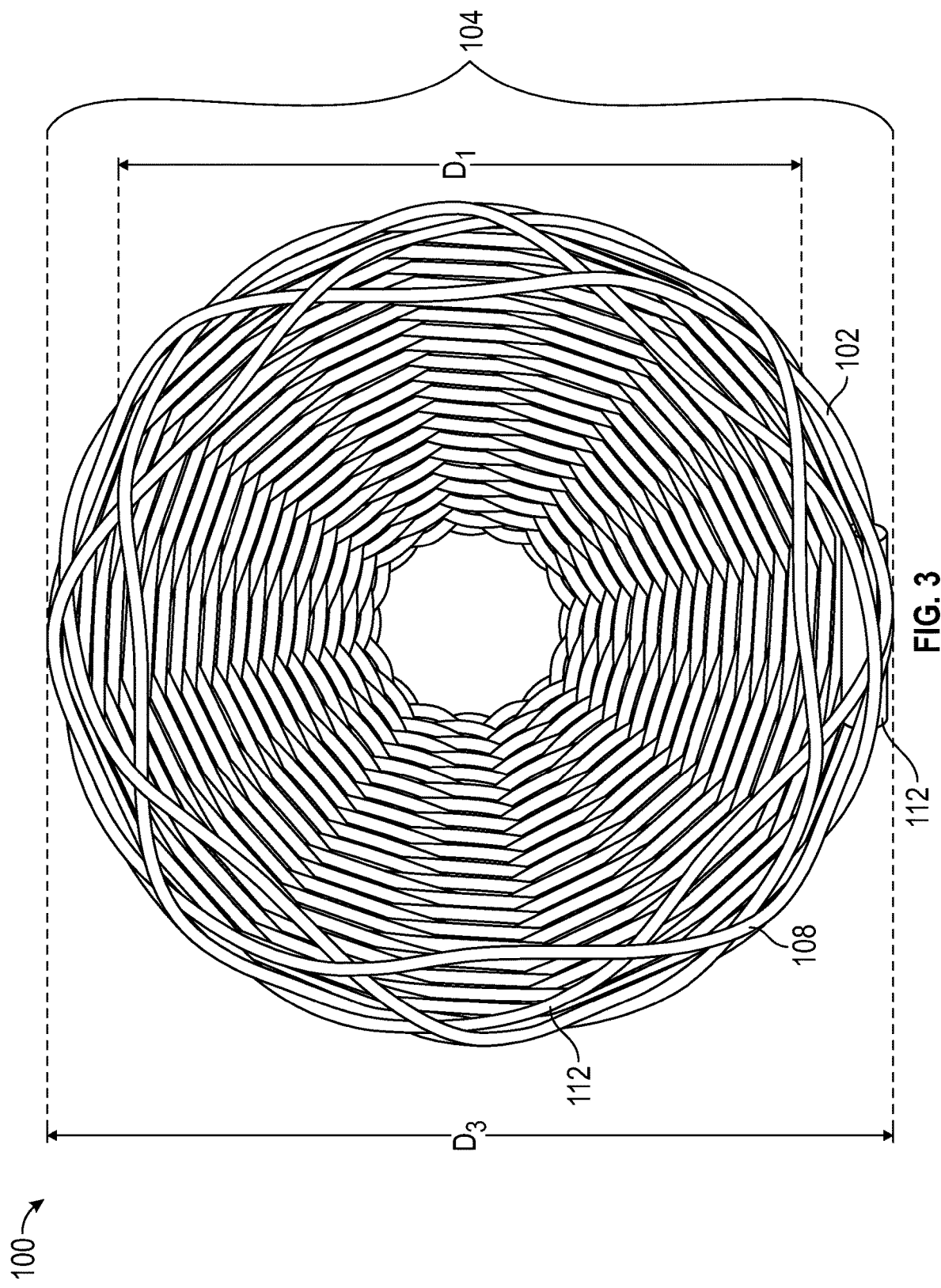
FIG. 3 is an end view from a proximal end of the implantable artificial bronchus shown in FIG. 1.

As shown in FIG. 3, maximum diameter $D_3$ of body 102 may be greater than diameter $D_1$ of proximal upper opening 104. Further, a portion of body 102 proximate to proximal upper opening 104 may taper towards central axis A of body 102 to allow for easy and efficient removal of implantable artificial bronchus 100 inside of the respiratory passageway. For example, a portion of body 102 proximate to proximal upper opening 104 being tapered towards central axis A of body 102 prevents any portion of body 102 proximate to proximal upper opening 104 from perforating lung tissue within a bronchi during insertion and placement of implantable artificial bronchus 100.

Body 102 may be a lattice structure comprised of woven wire or fiber. In one embodiment, body 102 is comprised of a single piece of wire or fiber 108. The single piece of fiber 108 may be arranged in a cross-weaving pattern to form a plurality of side openings 110. The ends of the single piece of fiber 108 may be connected and coupled together proximate the center of body 102 and the connection of the single piece of fiber 108 may be disposed within radiopaque marker 112. In some embodiments, the ends of the single piece of fiber 108 may be woven together proximate the center of body 102. For example, the ends of the single piece of fiber 108 may be woven together and disposed along first middle portion 122 or second middle portion 124. However, the ends of the single piece of fiber 108 may be coupled together at any location of body 102 or in other manners. The ends of the single piece of fiber 108 may be woven side-by-side, and may be going in opposite directions when woven together.

Although FIGS. 1 and 2 show fiber 108 being a single piece, fiber 108 may be composed of two or more strands of fiber. For example, body 108 may be comprised of two, three, four, or any number of fibers intertwined. Utilizing a plurality of fibers may increase the robustness of body 102 and reduce fatigue of body 102. In an embodiment, each fiber of the plurality of fibers may have a different diameter. For example, a fiber with a thicker diameter may be used for proximal portion 120 and first middle portion 122, and a fiber with a thinner diameter may be used for second middle portion 124 and distal portion 126. In an embodiment of the present invention, the multiple fibers may be arranged to be parallel to one another to comprise body 102. In another embodiment, the multiple fibers may be braided together to comprise body 102. As shown in FIGS. 1 and 2, fiber 108 of body 102 may be arranged in an alternating cross-weaving pattern creating a web-like structure However, fiber 108 of body 102 may be arranged in any other manner desired. For example, fiber 108 of body 102 may be arranged in a back braiding manner to provide a more rigid structure to maintain the shape of body 102.

According to an embodiment of the present invention, fiber 108 may be comprised of a thermoplastic polymer, such as polyether ether ketone (PEEK). In other embodiments, fiber 108 is comprised of one or more of polymer, metal, metal alloy, or stainless steel. Fiber 108 of body 102 may be made of a metal alloy having shape memory effect, such as NiTiNOL. However, fiber 108 may be a fiber of any other type of material such as a polymer, metal mesh, or any other type of material and may include a covering, such as silicone. In a preferred embodiment, fiber 108 of body 102 is comprised of a single fiber of PEEK. In some embodiments, fiber 108 of body 102 is comprised of PEEK and has a diameter of 0.30 mm. In an embodiment, fiber 108 of body 102 is made of a material having shape memory effect, such as PEEK. Fiber 108 may have a diameter between approximately 0.15 and approximately 0.40 mm. In a preferred, embodiment, fiber 108 has a thickness of approximately 0.25 mm. In an embodiment of the present invention, to create the structure of body 102, fiber 108 is woven over a tapered mandrel, which may be made of titanium, ceramic, tool steel, or stainless steel. The tapered mandrel includes a series of pins to hold fiber 108 in place. The tapered mandrel may have a small proximal diameter to form diameter $D_1$ and may include grooves for placement of fiber 108. Implantable artificial bronchus 100 may be manufactured by placing and weaving fiber 108 on the tapered mandrel to form body 102. In an embodiment, the woven assembly of fiber 108 is placed in a furnace to heat fiber 108 to a first temperature of approximately 140° and allowed to cool to set the shape of body 102 of implantable artificial bronchus 100. Implantable artificial bronchus 100 may then be placed on a second shaping form, such as another mandrel, and heated to a second temperature of approximately 170° to set the final shape of body 102. The first temperature and second temperature may vary based on the materials used.

Figure 5:
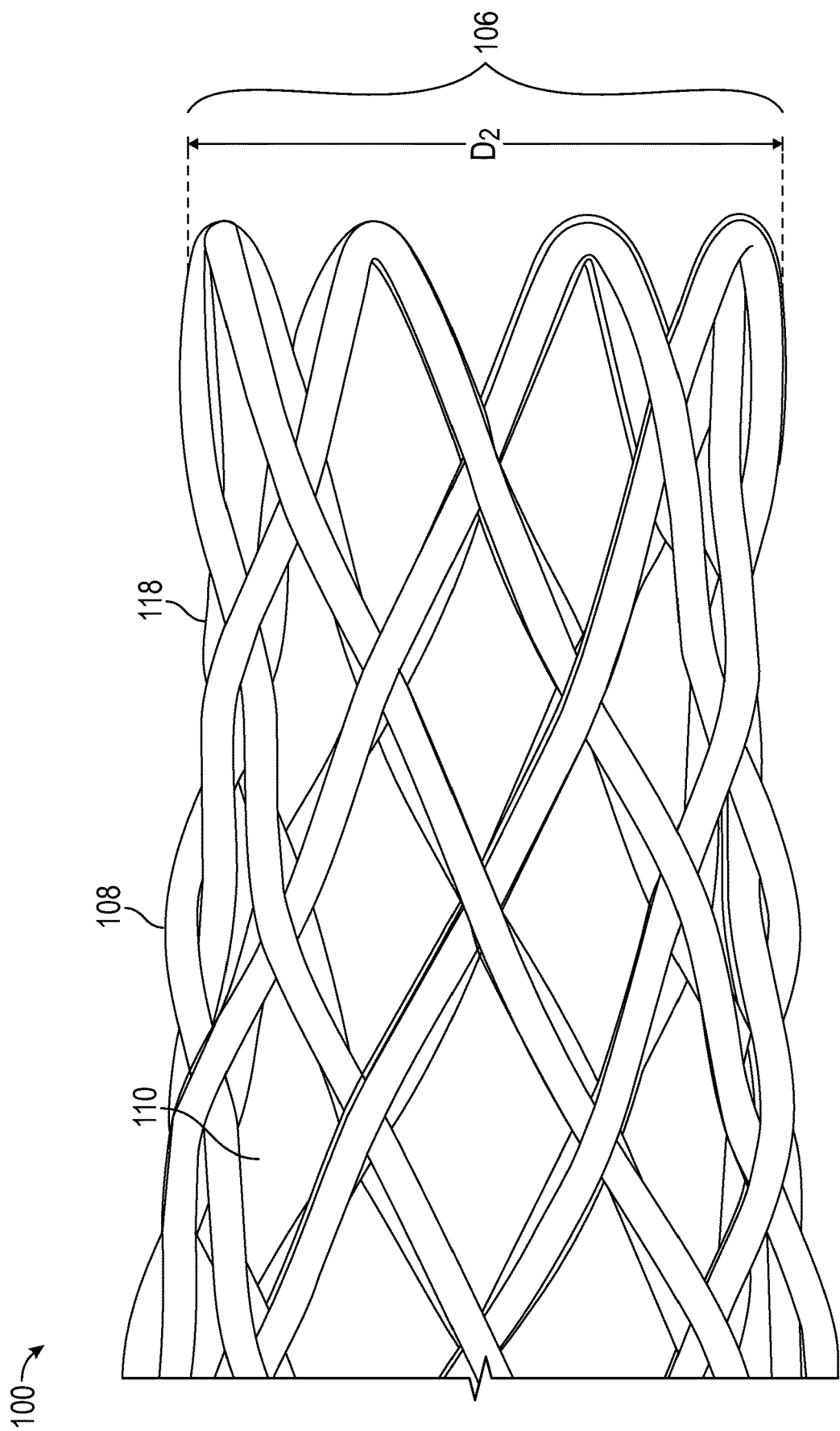
FIG. 5 is a close-up view of a distal end of the implantable artificial bronchus shown in FIG. 1.

In an embodiment of the present invention, as shown in FIG. 5, fiber 108 may include a conformal coating 118. In one embodiment, coating 118 may be a coating material comprised of silicone or other polymers. Fiber 108 may be coated with coating 118 prior to formation of the final shape of implantable artificial bronchus 100. Coating 118 may be configured to add protection to fiber 108, aid in biocompatibility of fiber 108, and reduce friction of fiber 108 against the lung tissue of the bronchi and bronchiole passageways to increase the ease of insertion of implantable artificial bronchus 100 within the respiratory passageway. Coating 118 may have a thickness between 0.05 mm and 0.1 mm.

With continued reference to FIGS. 1 and 2, body 102 may include side openings 110. Side openings 110 may be created due to the interweaving of fiber 108. Body 102 may be formed only by fiber 108 and may only include side openings 110 disposed along the length L of body 102. In one embodiment of the present invention, side openings 110 may be in direct contact with the surrounding tissue. For example, body 102 and implantable artificial bronchus 100 may not include any coverings or sheaths disposed around it, allowing side openings 110 to directly contact the surrounding walls of the bronchi and bronchioles. In practice, side openings 110 may be configured to allow air to enter and exit implantable artificial bronchus 100 through body 102. Side openings 110 of implantable artificial bronchus 100 may allow access to other respiratory passageways that branch off of the main respiratory passageway where implantable artificial bronchus 100 is deployed. These other respiratory passageways may be created due to collateral ventilation. As shown in FIGS. 1 and 2, side openings 110 may be disposed along the entire length L of body 102.

Side openings 110 may be disposed on body 102 proximate proximal upper opening 104 and proximate distal lower opening 106. Although FIGS. 1 and 2 show side openings 110 being diamond shaped, side openings 110 may be any shape desired depending on the cross-weaving pattern of fiber 108. In one embodiment, side opening 110 may include angles α and β created by the interweaving of fiber 108. Angles α and B may be between approximately 130° and approximately 20°. Angle α may be disposed proximate proximal upper opening 104 and angle β may be disposed proximate distal lower opening 106. Angle α may be greater than angle β. In some embodiments, angle α is less than 22° and angle β is greater than 130°. Angles α and β may decrease along length L of body 102 from proximal upper opening 104 to distal lower opening 106. In one embodiment, angle α is approximately 115° proximate to proximal upper opening 104 and angle β is approximately 22° proximate to distal lower opening 106. Decreasing angles α and β from proximal upper opening 104 to distal lower opening 106 results in body 102 being tapered along length L. In some embodiments, body 102 may include between 15 and 35 side openings 110 disposed along central axis A.

Figure 4:
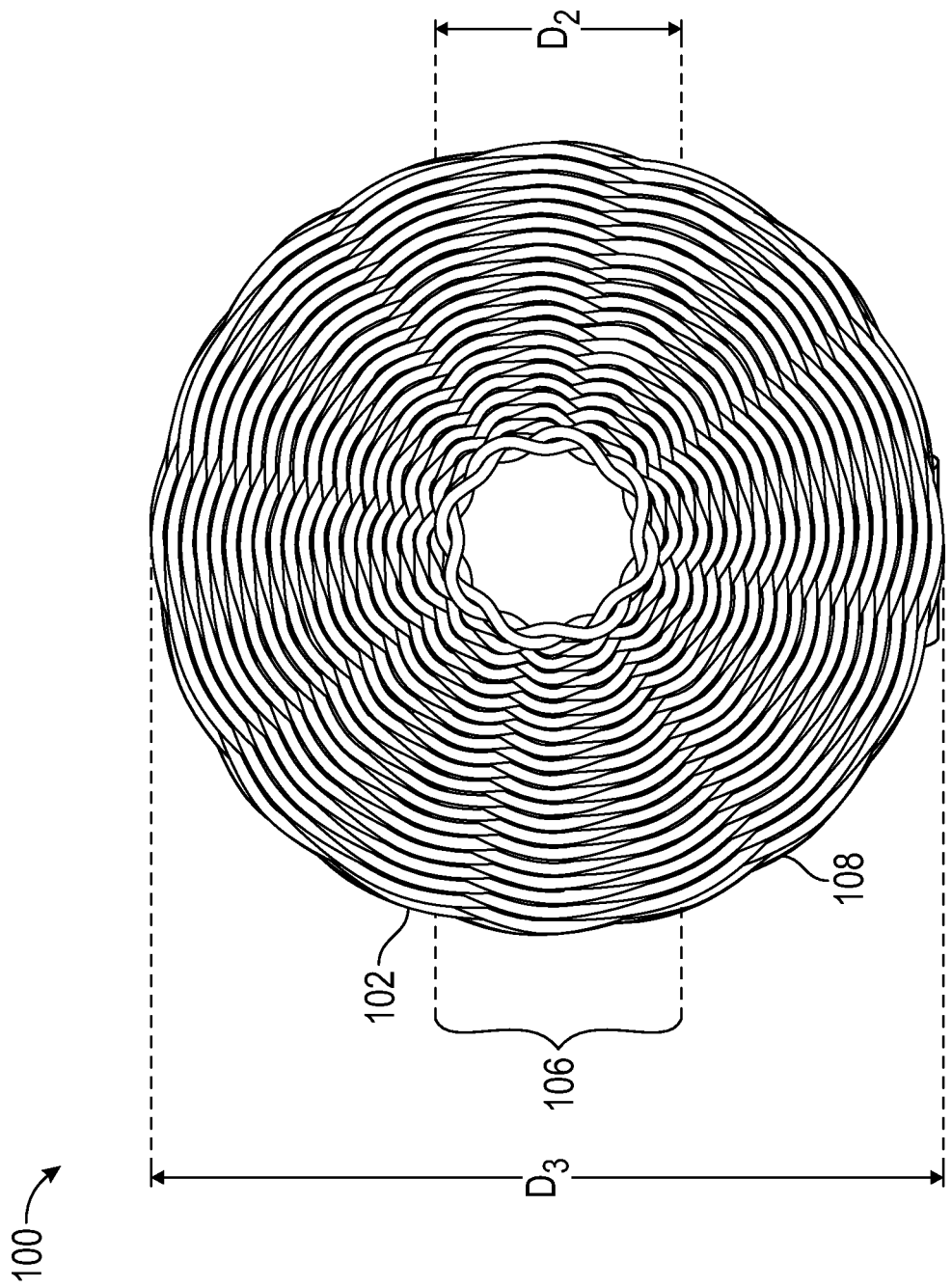
FIG. 4 is an end view from a distal end of the implantable artificial bronchus shown in FIG. 1.

Referring to FIG. 4, side openings 110 may not be visible when implantable artificial bronchus 100 is viewed from a distal end. For example, side openings 110 may be arranged along body 102 in a manner such than when implantable artificial bronchus 100 is viewed from a distal end, side openings 110 may not be visible to prevent or limit side openings 110 from engaging with surrounding tissue during insertion and implantation of implantable artificial bronchus 100.

Referring to FIGS. 1-4, implantable artificial bronchus 100 may include one or more radiopaque markers 112. One or more radiopaque markers 112 may be disposed at various locations of implantable artificial bronchus 100. For example, as shown in FIGS. 1-3, radiopaque marker 112 may be disposed on body 102 proximate proximal upper opening 104. However, radiopaque marker 112 may be disposed anywhere along body 102, such as proximal portion 120, first middle portion 122, second middle portion 124, or distal portion 126. Implantable artificial bronchus 100 may include any number of radiopaque markers 112 disposed along body 100. For example, implantable artificial bronchus 100 may include one, two, three, four, five, six, or any number of radiopaque markers 112 desired. Radiopaque marker 112 may be used with known imaging techniques and may be used to determine the placement of implantable artificial bronchus 100 and may also aid in the retrieval or removal of implantable artificial bronchus 100. In addition, radiopaque marker 112 may be used to determine the exact location of specific portions of implantable artificial bronchus 100 and body 102. For example, radiopaque marker 112 disposed on body 102 proximate proximal upper opening 104 may indicate to a user the location of the proximal end of implantable artificial bronchus 100 to determine proper alignment and location of implantable artificial bronchus 100. In an embodiment of the present invention, radiopaque marker 112 is disposed around fiber 108. As shown in FIG. 3, fiber 108 may be inserted through radiopaque marker 112. However, radiopaque marker 112 may be disposed on fiber 108, or underneath fiber 108.

Figure 6:
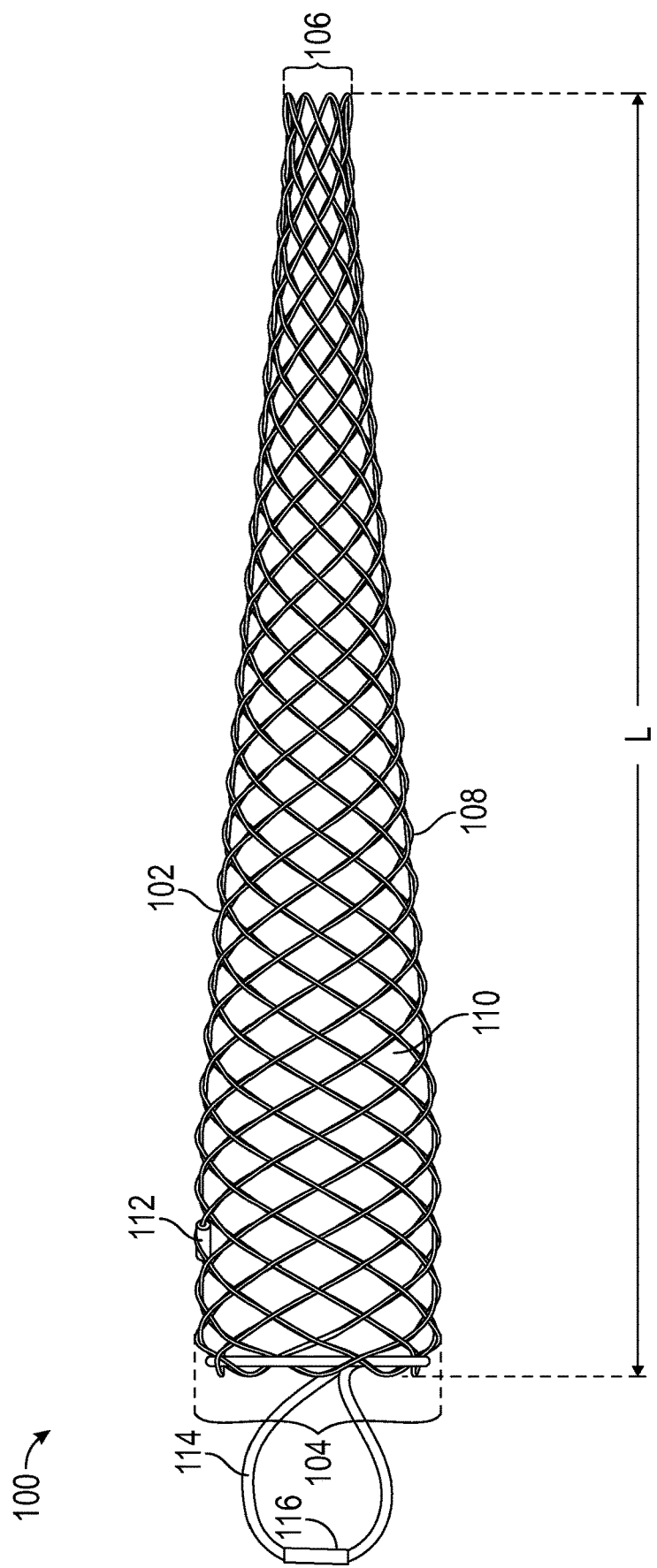
FIG. 6 is a side view of the implantable artificial bronchus of FIG. 1 shown having a retrieval loop.
Figure 7:
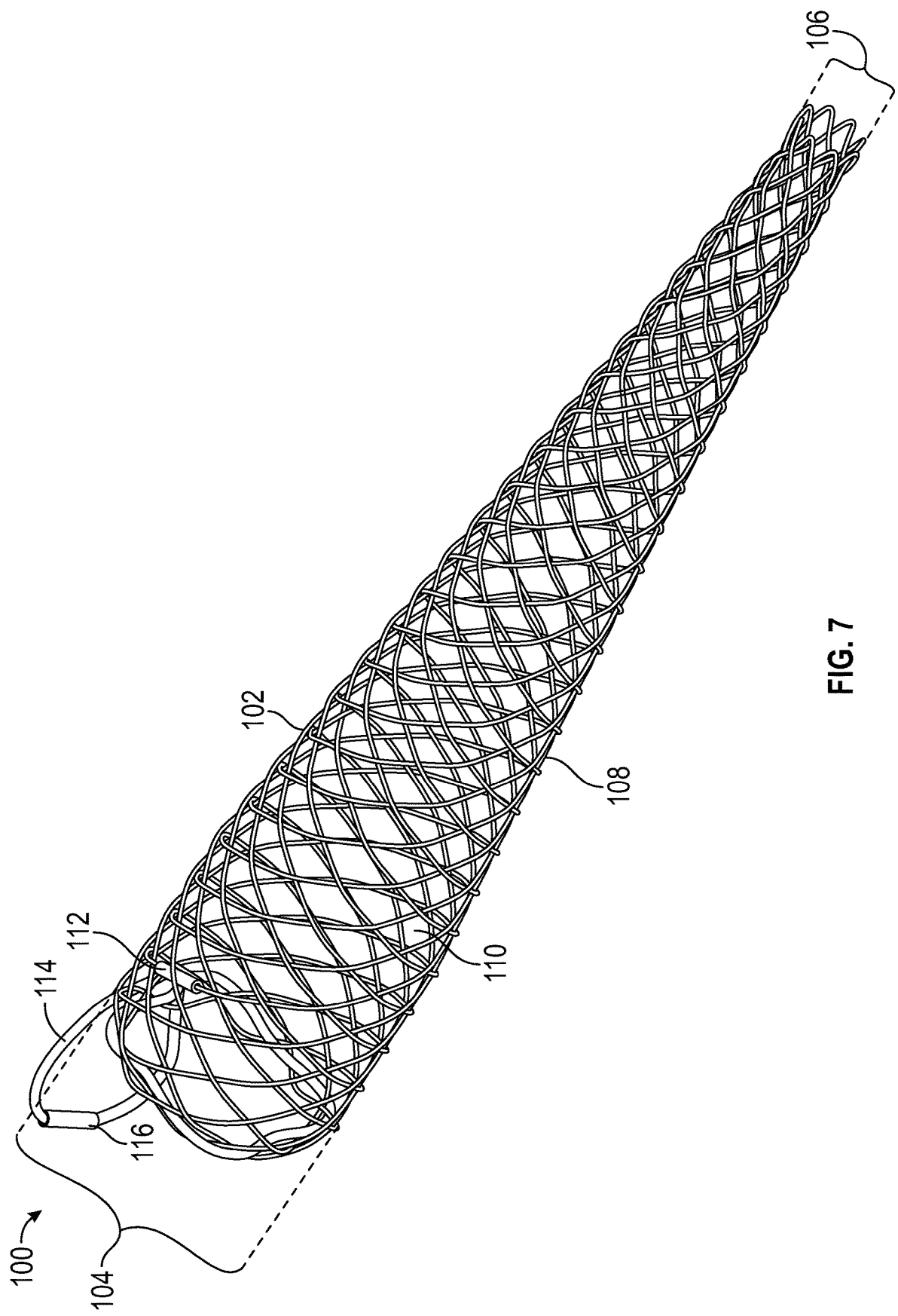
FIG. 7 is a perspective view the implantable artificial bronchus of shown in FIG. 6.

Referring to FIGS. 6 and 7, implantable artificial bronchus 100 may include one or more retrieval loops 114. Retrieval loop 114 may aid in the retrieval and removal of implantable artificial bronchus 100 from the respiratory passageways. In an embodiment of the present invention, retrieval loop 114 is integrated into body 102. For example, retrieval loop 114 may be configured to integrate into the cross-weaving pattern of fiber 108. Retrieval loop 114 may be integrated into body 102 near proximal upper opening 104. In another embodiment of the present invention, retrieval loop 114 is a separate structure coupled to body 102 as a secondary process. Retrieval loop 114 may be coupled to body 102 near proximal upper opening 104 or any other location along body 102. Although FIGS. 6 and 7 show implantable artificial bronchus 100 having one retrieval loop 114, implantable artificial bronchus 100 may have any number of retrieval loops 114. For example, implantable artificial bronchus 100 may have two, three, four or any number of retrieval loops 114 desired. Retrieval loop 114 may be made from a different material than fiber 108 of body 102 for increased robustness during retrieval and removal of implantable artificial bronchus 100. For example, retrieval loop 114 may be made from materials such as MP35N, 35N LT, 316L Stainless Steel, Titanium, polymers, suture materials, polypropylene, nylon, or any other material desired. Further, retrieval loop 114 may vary in diameter compared to fiber 108. In an embodiment, retrieval loop 114 may have a diameter of approximately 0.381 mm. However, retrieval loop 114 may have a diameter of any size desired. In an embodiment of the present invention, retrieval loop 114 includes handle 116. Handle 116 may be configured to allow a user to easily retrieve or remove implantable artificial bronchus 100 via retrieval loop 114. Handle 116 may be made of the same material as retrieval loop 114, or may be made of different materials to increase the overall strength of retrieval loop 114.

In some embodiments of the present invention, retrieval loop 114 include one or more radiopaque markers 112. The presence of one or more radiopaque markers 112 with retrieval loop 114 may assist in determining the location of retrieval loop 114 and/or implantable artificial bronchus 100, in addition to assisting in the retrieval of implantable artificial bronchus 100. In an embodiment of the present invention, retrieval loop 114 may be configured to be interwoven into body 102 and compressed along with body 102. Retrieval loop 114 being compressed allows for the entirety of implantable artificial bronchus 100 to be compressed for ease of insertion and implantation.

Figure 8:
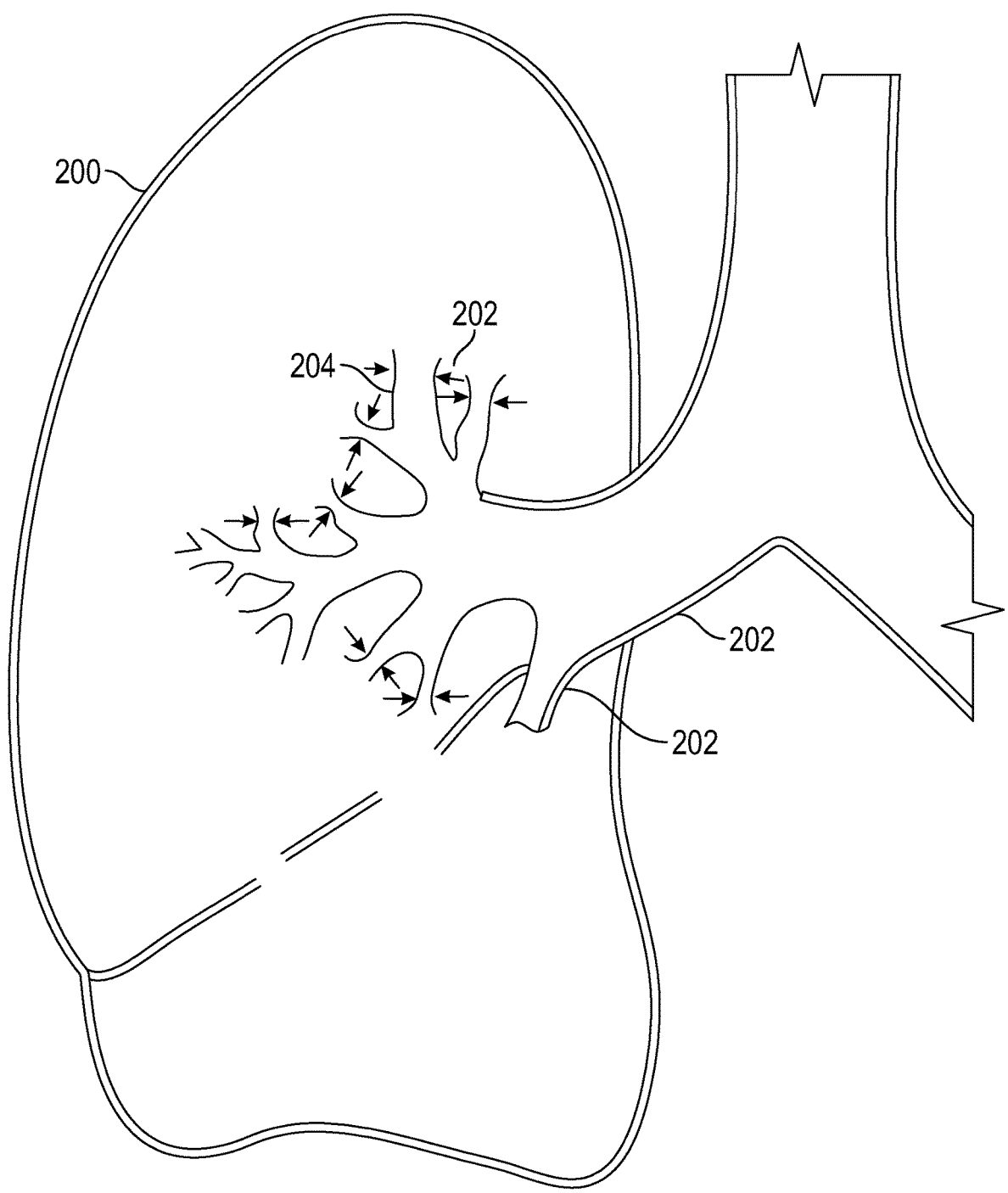
FIG. 8 is an illustration of a lung showing compressed branches.
Figure 9:
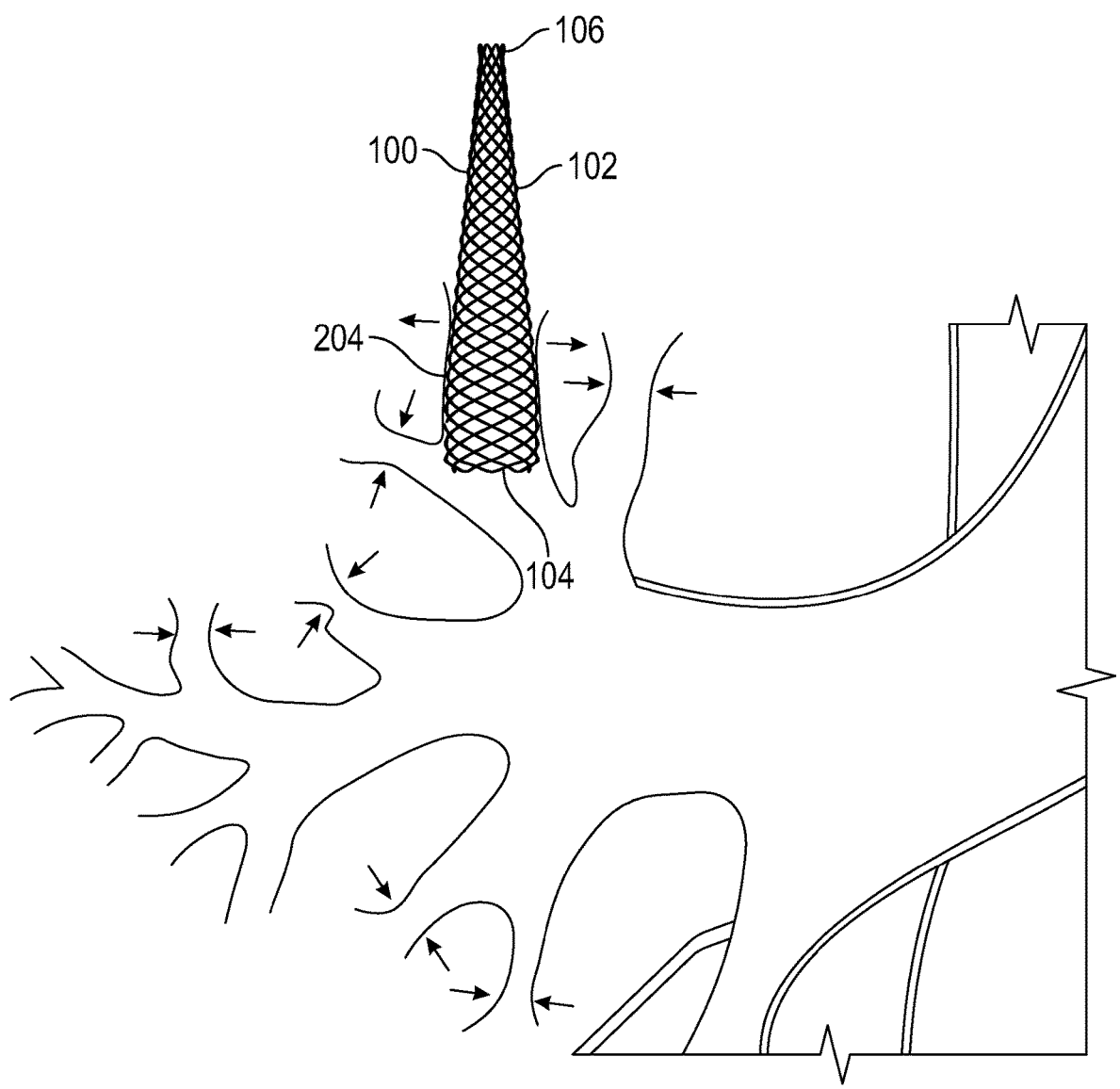
FIG. 9 is an illustration of an exemplary use of exemplary implantable artificial bronchus in accordance with one embodiment of the present invention.

In use, implantable artificial bronchus 100 may be used to promote lung disinsufflation. As shown in FIG. 8, lung 200 of an individual may include respiratory passageways 202 having walls 204. Respiratory passageways 202 may be bronchi or bronchioles, and walls 204 may be bronchi walls or bronchiole walls depending on the depth within respiratory passageway 202. In individuals with COPD and pulmonary emphysema, walls 204 of respiratory passageway 202 may be restricted limiting airflow, as denoted by the arrows in FIG. 8. Implantable artificial bronchus 100, as shown in FIG. 9, may be used to keep walls 204 of respiratory passageway 202 from restricting, allowing for airflow as depicted by the arrows in FIG. 9. Specifically, implantable artificial bronchus 100 may allow for air trapped within respiratory passageway 202 to exit by opening up, and keeping open, the bronchi and bronchioles.

Figure 10:
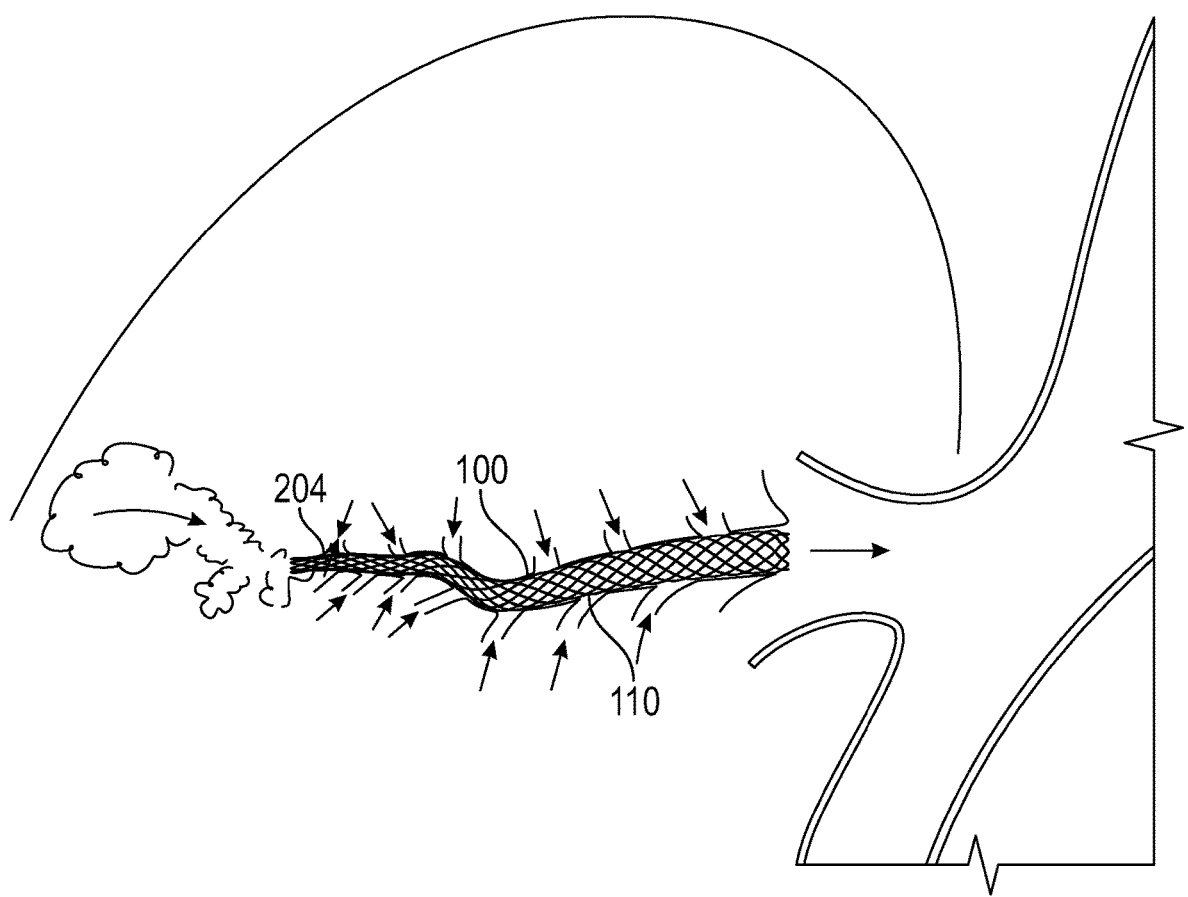
FIG. 10 is an illustration of an exemplary use of exemplary implantable artificial bronchus in accordance with one embodiment of the present invention.

Referring to FIGS. 9-10, in an embodiment, a surgeon places implantable artificial bronchus 100 into the respiratory passageway by inserting a catheter distally into a respiratory passageway of the lung. The catheter may contain implantable artificial bronchus 100 which may be compressed within the catheter. For example, implantable artificial bronchus 100 may be compressed radially toward central axis A reducing the diameter of implantable artificial bronchus 100 to fit implantable artificial bronchus 100 within the catheter during insertion and implantation. The catheter may be withdrawn proximally relative to implantable artificial bronchus 100, unsheathing implantable artificial bronchus 100 and causing it to naturally expand and remain in the respiratory passageway. In another embodiment of the present invention, implantable artificial bronchus 100 is coupled to a bronchoscope for placement of implantable artificial bronchus 100 within respiratory passageways. In a preferred embodiment, implantable artificial bronchus 100 is composed of a material such as PEEK that allows implantable artificial bronchus 100 to expand to its original shape. As shown in FIG. 9, implantable artificial bronchus 100 within the respiratory passageways may be configured to promote enlargement of the bronchial passageway and in turn cause lung deflation.

In an embodiment of the present invention, the insertion of implantable artificial bronchus 100 into respiratory passageway 202 is done with a channel bronchoscope. For example, a 2.8 mm channel bronchoscope may be used to assist with the insertion and implantation of implantable artificial bronchus 100 into respiratory passageway 202. In an embodiment, the bronchoscope assists with delivering implantable artificial bronchus 100 to level 15 of the respiratory bronchioles. As implantable artificial bronchus 100 expands from its compressed state, implantable artificial bronchus 100 may be able to reach deeper respiratory bronchioles, such has levels 17, 18, or 19. For example, implantable artificial bronchus 100 may be placed within the distal bronchus having a diameter between 2-2.5 mm, and maximum diameter $D_3$ of implantable artificial bronchus 100 may allow implantable artificial bronchus 100 to support bronchus wall 204 such that bronchus wall 204 does not collapse and close off the airway. Further, implantable artificial bronchus 100 may be inserted into respiratory passageway 202 located in distal portions via access through the central airway. The implant path may be initially identified with a malleable metal guide. A subsequent catheter passage may be done to guide implantable artificial bronchus 100 in a compressed state. However, compressed implantable artificial bronchus 100 may be introduced directly by a guidewire.

Referring to FIG. 10, implantable artificial bronchus 100 may be flexible to allow for body 102 of implantable artificial bronchus 100 to conform to the shape of a respiratory passageway. For example, implantable artificial bronchus 100 may be configured to weave back and forth as it enters distal bronchioles. In an embodiment, body 102 is configured to curve in a first radial direction along a first length of body 102 and a second radial direction opposite the first radial direction along a second length of body 102. Implantable artificial bronchus 100 may be configured to be flexible due to the interweaving of fiber 108 of PEEK. For example, body 102 may be comprised of a single interweaving fiber 108, which allows various segments of fiber 108 to cross and slide over one another during movement of implantable artificial bronchus 100. In an embodiment, implantable artificial bronchus 100 does not include any element to couple the various segments of fiber 108, thereby allowing them to move and slide over one another, increasing the flexibility of implantable artificial bronchus 100. The flexibility of implantable artificial bronchus 100 and body 102 allow for implantable artificial bronchus 100 to conform and be secured within a respiratory passageway without causing damage to the surrounding tissues. In addition, the flexibility allows for a single implantable artificial bronchus 100 to be used in a longer respiratory passageway instead of using multiple implantable artificial bronchi. Further, the flexibility of implantable artificial bronchus 100 allows it to reach respiratory bronchioles beyond level 15. Implantable artificial bronchus 100 may be configured to provide structure to bronchus wall 204 while allowing air trapped within in distal alveoli to exit via the central airway. The shape and flexibility of implantable artificial bronchus 100 allows implantable artificial bronchus 100 to reach as close as possible to distal respiratory bronchioles, such as respiratory bronchioles beyond level 15 and close to alveoli (>15 levels).

In an embodiment, side openings 110 of body 102 allow for air to enter body 102 while implantable artificial bronchus 100 is disposed within the respiratory passageway. For example, as denoted by the arrows in FIG. 10, air may enter body 102 via side openings 110 from smaller side respiratory passageways. These smaller side respiratory passageways may be created due to collateral ventilation. This allows air to flow through body 102 from distal bronchioles while implantable artificial bronchus 100 is implanted in the respiratory passageway.

Referring to FIGS. 11A-B, a measuring catheter 400 may be used prior to insertion of implantable artificial bronchus 100 into the respiratory passageway. Measuring catheter 400 may be inserted into a channel bronchoscope to determine the depth of the desired target site within the respiratory passageway. Measuring catheter 400 may be a steerable wire that may be inserted into the channel bronchoscope prior to delivery of implantable artificial bronchus 100. For example, measuring catheter 400 may have a fixed diameter of about 2 mm. The diameter of measuring catheter may be approximately 2 mm to prevent insertion beyond bronchioles that have a diameter less than 2 mm. Measuring catheter 400 having a fixed diameter of approximately 2 mm allows measuring catheter 400 to measure the distance to where the bronchioles narrows to approximately 2 mm. Measuring catheter 400 may include distal 406, proximal end 404, and handle 402. Distal end 406 and proximal end 404 may include markers 403. Markers 403 may be located at predefined intervals and may be visualized using a camera of the channel bronchoscope to determine the depth and space available to implant implantable artificial bronchus 100 within the respiratory passageway. In an embodiment, markers 403 at distal end 406 and the interval at which they are located are identical to markers 403 at proximal end 404. This allows the user to determine the depth without solely relying on the camera since proximal end 404 may be located outside of the channel bronchoscope. Handle 402 may be a molded plastic handle and may be used for manipulating measuring catheter 400. In an embodiment, handle 402 is glued in place by backfilling a hole within handle 402 with an adhesive.

Referring to FIGS. 12A-D, a delivery device 300 may be used to delivery implantable artificial bronchus 100. Once the depth is determined via measuring catheter 400, delivery device 300 may be used to deliver implantable artificial bronchus 100 to the target site. Delivery device 300 may include delivery portion 301 and handle 310. Delivery portion 301 may include outer sheath 302, delivery wire 304, and stabilizer 308. Handle 310 may be coupled to delivery portion 301 at distal end 313 of handle 310. Implantable artificial bronchus 100 may be inserted into delivery portion 301 and disposed within delivery device 300 for delivery to a target site within the respiratory passageway. For example, delivery device 300 may be inserted within a working channel of the bronchoscope. Delivery portion 301 may be inserted and advanced into the respiratory passageway. Once delivery portion 301 has reached the target site for delivering implantable artificial bronchus 100, outer sheath 302 may be retracted to expose delivery wire 304 and implantable artificial bronchus 100, allowing for the delivery of implantable artificial bronchus 100 at the target site. Delivery portion 301 may then be removed from the working channel of the bronchoscope.

Handle 310 may include actuator 312, stabilizer 308, proximal end 311, distal end 313, anchor 316, and outer surface 317. Actuator 312 may be disposed on outer surface 317. In an embodiment, actuator 312 may be disposed within slot 319 on outer surface 317. Actuator 312 may be actuated via a thumb of a user to slide actuator 312 from proximal end 311 to distal end 313. Actuator 312 may be coupled to outer sheath 302 and may be configured to retract outer sheath 302 into handle 310 to expose delivery wire 304. For example, actuator 312 may be coupled to a portion of outer sheath 302 disposed within handle 310, thereby resulting in outer sheath 302 being retracted into handle 310 when actuator 312 is moved towards proximal end 311. Outer sheath 302 may pass through stabilizer 308 to assist in securing outer sheath 302 to handle 310. In an embodiment, outer sheath 302 is movable relative to stabilizer 308 and handle 310. Outer sheath 302 may include distal end 315, slot 307, and marker 318, and may be coupled to distal end 313 of handle 310. Marker 318 may be used to help determine various locations of outer sheath 302 within the respiratory passageway. Delivery wire 304 may be disposed within outer sheath 302 and may be comprised of a rigid material. Delivery wire 304 may extend from proximal end 311 of handle 310 to distal end 315 of outer sheath 302. Delivery wire 304 may be anchored to proximal end 311 at anchor 316 of handle 310. Anchor 316 may be configured to secure delivery wire 304 such that outer sheath 302 may be movable relative to delivery wire 304. Delivery wire 304 may include stopper 305, which may be disposed at the end of delivery wire 304. Stopper 305 may be disposed within outer sheath 302 proximate to slot 307.

In an embodiment, implantable artificial bronchus 100 is inserted into distal end 315 of outer sheath 302, proximate to slot 307, which is proximate stopper 305 of delivery wire 304. Slot 307 may be located proximate distal end 315 of outer sheath 302. Implantable artificial bronchus 100 may be inserted into distal end 315 by threading a suture through a loop of proximal upper opening 104. The ends of the suture may pass through a funnel, into outer sheath 302, and out of slot 307. Implantable artificial bronchus 100 is inserted into distal end 315 of outer sheath 302 by pulling on the ends of the suture, which pull implantable bronchus 100 through the funnel resulting in collapsing implantable artificial bronchus 100. Continued pulling of the ends of the suture pulls collapsed implantable artificial bronchus 100 into distal end 315 of outer sheath 302. The suture is pulled until implantable artificial bronchus 100 reaches slot 307, which is proximate stopper 305 of delivery wire 304. The suture may then be pulled through slot 307 and removed from implantable artificial bronchus 100. Once implantable artificial bronchus 100 is inserted into outer sheath 302, implantable artificial bronchus 100 may expand. For example, body 102 of implantable artificial bronchus 100 having length L of approximately 50 mm may expand to have length L of approximately 80 mm within outer sheath 302. By way of another example, body 102 of implantable artificial bronchus 100 having length L of approximately 80 mm may expand to have length L of approximately 128 mm within outer sheath 302. During initial insertion, implantable artificial bronchus 100 may reduce down to its intended length. Once implantable artificial bronchus 100 is inserted into outer sheath 302 of delivery portion 301, outer sheath 302 may be inserted into a working channel of the bronchoscope.

Delivery portion 301 may be inserted into the respiratory passageway and advanced to the target site. Once the target site has been reached, actuator 312 may be moved towards proximal end 311 of handle 310, thereby retracting outer sheath 302 into handle 310 and exposing delivery wire 304, stopper 305, and implantable artificial bronchus 100. Retracting of outer sheath 302 does not cause movement of implantable artificial bronchus 100 towards handle 310 due to delivery wire 304 and stopper 305 exerting a force on implantable artificial bronchus 100 preventing movement of implantable artificial bronchus 100. Once outer sheath 302 has been retracted and implantable artificial bronchus 100 is exposed, implantable artificial bronchus 100 may expand to its original position within the respiratory passageway. Delivery portion 301 of delivery device 300 may then be withdrawn from the respiratory passageway via the working channel of the bronchoscope.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. The words "proximal", "distal", "upper" and "lower" designate directions in the drawings to which reference is made. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

What is claimed is:

1. An implantable artificial bronchus comprising:
a body comprised of one or more fibers woven together forming a lattice structure, the body having a proximal upper opening and a distal lower opening in fluid communication with the proximal upper opening, the body at least partially tapering along a length of the body toward the distal lower opening and having a plurality of side openings configured to allow air to enter into and exit the implantable artificial bronchus through the body, wherein the proximal upper opening includes a woven portion defining the proximal upper opening, the woven portion tapering radially inwards;
wherein a length of the body is greater than 4 times a largest diameter of the body,
wherein a diameter of the proximal upper opening is larger than a diameter of the distal lower opening, and
wherein the plurality of side openings include a first side opening proximate the proximal upper opening and a second side opening proximate the distal lower opening, the first side opening having a first angle and the second side opening having a second angle less than the first angle.

2. The implantable artificial bronchus of claim 1, wherein the body includes a proximal portion, a first middle portion, a second middle portion, and a distal portion, the proximal portion being tapered towards a central axis of the body.

3. The implantable artificial bronchus of claim 2, wherein the first middle portion and the second middle portion are disposed between the proximal portion and the distal portion, the first middle portion being proximate the proximal portion and the second middle portion being proximate the distal portion, the first middle portion having a first taper and the second middle portion having a second taper, the second taper being larger than the first taper.

4. The implantable artificial bronchus of claim 2, wherein a diameter of the first middle portion is greater than a diameter of the proximal portion, a diameter of the second middle portion, and a diameter of the distal portion.

5. The implantable artificial bronchus of claim 4, wherein the diameter of the distal portion is less than the diameter of the proximal portion, the diameter of the first middle portion, and the diameter of the second middle portion.

6. The implantable artificial bronchus of claim 4, wherein the diameter of the first middle portion is equal to or less than the largest diameter of the body.

7. The implantable artificial bronchus of claim 4, wherein the diameter of the second middle portion constantly decreases along the length of the body from the first middle portion to the distal portion.

8. The implantable artificial bronchus of claim 4, wherein the diameter of the distal portion is substantially the same proximate the second middle portion and proximate distal lower opening.

9. The implantable artificial bronchus of claim 2, wherein the proximal portion flares out from the proximal upper opening to the first middle portion.

10. The implantable artificial bronchus of claim 1, wherein the maximum diameter of the body is greater than the diameter of the proximal upper opening.

11. The implantable artificial bronchus of claim 1, wherein the body is a web comprised of a single fiber forming the lattice structure, the single fiber having ends woven together proximate a middle portion of the body.

12. The implantable artificial bronchus of claim 11, wherein the single fiber is coated with at least one of silicone or polymer.

13. The implantable artificial bronchus of claim 1, wherein the diameter of the proximal upper opening is greater than twice the diameter of the distal lower opening.

14. The implantable artificial bronchus of claim 1, wherein in an implanted state the body is configured to curve in a first radial direction along a first length of the body and a second radial direction opposite the first radial direction along a second length of the body.

15. The implantable artificial bronchus of claim 1, wherein the plurality of side openings include an angle ranging between approximately 130° proximate the proximal upper opening and 20° proximate the distal lower opening.

16. The implantable artificial bronchus of claim 1 further comprising:

at least one retrieval loop coupled to the body at the proximal upper opening.

17. The implantable artificial bronchus of claim 16, wherein the at least one retrieval loop extends from the proximal upper opening in a direction substantially parallel to a central axis of the body.

18. The implantable artificial bronchus of claim 1 further comprising:
at least one radiopaque marker disposed on the body.

19. The implantable artificial bronchus of claim 1, wherein the body has a maximum diameter of is approximately 6 mm to approximately 12 mm.

20. The implantable artificial bronchus of claim 1, wherein the body is comprised of PEEK.

21. The implantable artificial bronchus of claim 1, wherein the body is comprised of NiTiNOL.

22. The implantable artificial bronchus of claim 1, wherein the body includes a single fiber arranged in an alternating cross-weaving pattern.

23. The implantable artificial bronchus of claim 1, wherein the implantable artificial bronchus does not include a valve or a nozzle coupled to the body.

24. The implantable artificial bronchus of claim 1, wherein the woven portion has a diameter that is less than a maximum diameter of the body.

25. The implantable artificial bronchus of claim 1, wherein the woven portion includes a plurality of openings positioned circumferentially around a central axis of the body.

26. The implantable artificial bronchus of claim 1, wherein the first angle and the second angle are disposed along a central axis of the body, the central axis extending along a length of the body.

27. An implantable artificial bronchus comprising:
a body comprised of one or more fibers woven together forming a lattice structure, the body having a proximal upper opening and a distal lower opening in fluid communication with the proximal upper opening, the proximal upper opening tapering towards a central axis of the body, and the body constantly tapering from a portion proximate the proximal upper opening toward a portion proximate the distal lower opening, and having a plurality of side openings configured to allow air to enter into and exit the implantable artificial bronchus through the body, the body comprising:
a proximal portion being tapered toward a central axis of the body;
a first middle portion having a first middle taper;
a second middle portion having a second middle taper larger than the first middle taper; and
a distal portion having a constant distal diameter, wherein the first middle portion and the second middle portion are disposed between the proximal portion and the distal portion;
wherein a diameter of the proximal upper opening is at least twice as large as a diameter of distal lower opening, and the diameter of the proximal upper opening is less than a maximum diameter of the body, the maximum diameter of the body being proximate the proximal upper opening,
wherein the proximal upper opening includes a woven portion defining the proximal upper opening, the woven portion tapering radially inwards, and
wherein in an implanted state the body is configured to curve in a first radial direction along a first length of the body and a second radial direction opposite the first radial direction along a second length of the body,
wherein the plurality of side openings include a first side opening proximate the proximal upper opening and a second side opening proximate the distal lower opening, the first side opening having a first angle and the second side opening having a second angle less than the first angle.

28. A method of delivering an implantable artificial bronchus to an air passageway, the method comprising:
inserting the implantable artificial bronchus into a delivery device, the delivery device comprising:
a handle having a proximal end, a distal end, an outer surface, and an actuator movable about the outer surface;
a delivery portion including an outer sheath and a delivery wire, the outer sheath coupled to the actuator of the handle and extending out of the distal end of the handle, the outer sheath having a distal end and at least one slot, wherein the implantable artificial bronchus is inserted into the delivery device via the distal end; and
the delivery wire coupled to a proximal end of the handle and extending out of the distal end of the handle and into the outer sheath such that the delivery wire is disposed within the outer sheath, the delivery wire including a stopping member, wherein the stopping member is disposed proximate the implantable artificial bronchus after insertion of the implantable artificial bronchus into the delivery device;
inserting the delivery portion of the delivery device into a bronchoscope such that the outer sheath is disposed within a working channel of the bronchoscope;
advancing the delivery portion through a bronchial passage via the bronchoscope;
retracting the outer sheath, via the actuator, exposing the delivery wire and the implantable artificial bronchus, causing the implantable artificial bronchus to naturally expand and remain in the bronchial passage; and
removing the delivery device from the bronchial passage through the working channel of the bronchoscope,
wherein the implantable artificial bronchus comprises:
a body having a proximal upper opening and a distal lower opening in fluid communication with the proximal upper opening, the body at least partially tapering along a length of the body toward the distal lower opening and having a plurality of side openings configured to allow air to enter into and exit the implantable artificial bronchus through the body,
wherein a length of the body is greater than 4 times a largest diameter of the body, and
wherein a diameter of the proximal upper opening is larger than a diameter of the distal lower opening.

29. The method of delivering an implantable artificial bronchus of claim 28, wherein inserting the implantable artificial bronchus into the delivery device comprises:
threading a suture through at least one proximal loop of the implantable artificial bronchus;
pulling on the suture to cause the implantable artificial bronchus to collapse;
inserting the suture and the implantable artificial bronchus through the distal end of the outer sheath; and
removing the suture from the implantable artificial bronchus and the delivery device, via the at least one slot, such that the implantable artificial bronchus remains in the delivery device.

* * * * *